(12) United States Patent
Poffenberger et al.

(10) Patent No.: US 9,706,771 B2
(45) Date of Patent: Jul. 18, 2017

(54) AGROCHEMICAL OIL COMPOSITIONS COMPRISING ALKYLPOLYSILOXANE ADJUVANTS OF HIGH SILICONE CHARACTER

(75) Inventors: Craig Poffenberger, Chesterfied, VA (US); David Lindsay, Chester, VA (US); Jörg Simpelkamp, Richmond, VA (US); Christian Hartung, Essen (DE); Michael Ferenz, Essen (DE)

(73) Assignee: Evonik Degussa GmbH, Essen (DE)

( * ) Notice: Subject to any disclaimer, the term of this patent is extended or adjusted under 35 U.S.C. 154(b) by 439 days.

(21) Appl. No.: 13/124,522

(22) PCT Filed: Sep. 3, 2009

(86) PCT No.: PCT/EP2009/061385
§ 371 (c)(1),
(2), (4) Date: Jun. 27, 2011

(87) PCT Pub. No.: WO2010/043447
PCT Pub. Date: Apr. 22, 2010

(65) Prior Publication Data
US 2011/0251070 A1    Oct. 13, 2011

Related U.S. Application Data

(60) Provisional application No. 61/106,307, filed on Oct. 17, 2008.

(51) Int. Cl.
*A01N 25/30* (2006.01)
*A01N 25/04* (2006.01)
*B01F 17/54* (2006.01)

(52) U.S. Cl.
CPC ............. *A01N 25/30* (2013.01); *A01N 25/04* (2013.01); *B01F 17/0071* (2013.01)

(58) Field of Classification Search
USPC ........................................ 504/358, 362, 101
See application file for complete search history.

(56) References Cited

U.S. PATENT DOCUMENTS

| | | | |
|---|---|---|---|
| 6,211,139 B1 | 4/2001 | Dalrymple et al. | |
| 6,414,175 B1 | 7/2002 | Burkhart et al. | |
| 6,458,343 B1 | 10/2002 | Deac et al. | |
| 6,669,949 B2 | 12/2003 | Wilkowski et al. | |
| 6,730,749 B1 | 5/2004 | Burkhart et al. | |
| 6,734,141 B2 | 5/2004 | Simpelkamp et al. | |
| 7,635,581 B2 | 12/2009 | Thum et al. | |
| 7,727,599 B2 | 6/2010 | Venzmer et al. | |
| 8,158,572 B2 | 4/2012 | Schubert et al. | |
| 2001/0039321 A1 | 11/2001 | Kennedy et al. | |
| 2005/0244357 A1 | 11/2005 | Sieverding et al. | |
| 2006/0155090 A1 | 7/2006 | Ferenz | |
| 2006/0188455 A1 | 8/2006 | Ferenz et al. | |
| 2007/0213226 A1 | 9/2007 | Sieverding et al. | |
| 2008/0027202 A1 | 1/2008 | Herrwerth et al. | |
| 2008/0305065 A1 | 12/2008 | Ferenz et al. | |
| 2009/0062459 A1 | 3/2009 | Ferenz et al. | |
| 2009/0138306 A1 | 11/2009 | Meyer et al. | |
| 2010/0034765 A1 | 2/2010 | Winter et al. | |
| 2010/0041629 A1 | 2/2010 | Lindsay et al. | |
| 2010/0055760 A1 | 3/2010 | Ferenz et al. | |
| 2010/0056649 A1 | 3/2010 | Ferenz et al. | |
| 2010/0056818 A1 | 3/2010 | Thum et al. | |
| 2010/0081763 A1 | 4/2010 | Meyer et al. | |
| 2010/0248325 A1 | 9/2010 | Eckstein et al. | |
| 2010/0266651 A1 | 10/2010 | Hartung et al. | |
| 2011/0070175 A1 | 3/2011 | Ferenz et al. | |

FOREIGN PATENT DOCUMENTS

| | | | |
|---|---|---|---|
| EP | 529 847 | 3/1993 | |
| EP | 0648413 | * 10/1994 | ............ A01N 35/30 |
| EP | 648 413 | 4/1995 | |
| EP | 1 679 335 | 7/2006 | |
| WO | 01/49114 | 7/2001 | |
| WO | 2009-138306 | 11/2009 | |

OTHER PUBLICATIONS

Stevens, P. J. G. "Organosilicone Surfactants as Adjuvants for Agrochemicals", Pesticide Science, Elsevier, vol. 38, No. 2/3, Jan. 1, 1993, pp. 103-122.

* cited by examiner

*Primary Examiner* — Ali Soroush
*Assistant Examiner* — Danielle Sullivan
(74) *Attorney, Agent, or Firm* — Haug Partners LLP

(57) ABSTRACT

The invention relates to agrochemical compositions comprising oils and alkylpolysiloxanes of high silicone character (HSCAS) with good oil compatibility which improve the spreading behavior and reduce surface tension of oil-based agricultural formulations, and optionally comprising agrochemically active ingredients such as fungicides, insecticides or herbicides and/or inert ingredients such as emulsifiers and other agrochemically acceptable components.

20 Claims, No Drawings

AGROCHEMICAL OIL COMPOSITIONS COMPRISING ALKYLPOLYSILOXANE ADJUVANTS OF HIGH SILICONE CHARACTER

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

FIELD OF THE INVENTION

The invention relates to agrochemical compositions comprising oils and alkylpolysiloxanes of high silicone character (HSCAS) with good oil compatibility which improve the spreading behavior and reduce surface tension of oil-based agricultural formulations, and optionally comprising agrochemically active ingredients such as fungicides, insecticides or herbicides and/or inert ingredients such as emulsifiers and other agrochemically acceptable components.

OBJECT OF THE INVENTION

Improving the spreading coverage of agricultural sprays on plant surfaces is desirable and well known as beneficial to the efficacy of agricultural treatments. It is particularly desirable that agricultural pesticide sprays applied to plants are rapidly and uniformly distributed in order to improve protection and enhance penetration of the active ingredient into the plant, therefore gaining improved coverage and adhesion, to control unwanted weeds, insect and mite infestations, and to control plant diseases.

As many pesticides have limited water solubility, oils often serve as the carriers to deliver the active ingredient to the target plant or pest. The increasing cost of oils, problems with phytotoxicity and environmental concerns related to pesticidal compositions create a pressure to reduce the use of spray oils, which is however not possible due to the critical role they play in the agricultural spray formulation.

It is therefore desired to have adjuvants which can reduce the bulk surface tension of liquid oil-containing sprays, and, thereby improving the wetting and spreading of the oils and active ingredients, and therefore allowing for reduction of the amount of spray oils.

BACKGROUND OF THE INVENTION

For the agrochemical compositions of the invention, the alkylpolysiloxanes of high silicone character (HSCAS) contained therein are defined herein as having blocks of unmodified polydimethylsiloxane segments in their molecular structure, i.e. at least 10 uninterrupted D groups ($-Me_2SiO-$) on average, and having hydrocarbon radicals providing good compatibility with the oil.

The HSCAS reduce the surface tension of the agricultural spray oils and improve the spread coverage on foliage, including those leaves with hydrophobic surfaces and/or corrugated surfaces or those which are positioned other than horizontally, thereby enhancing the performance of the agrochemical compositions. However, the state of the art had not taught the use of HSCAS in agrochemical compositions.

In 1993, Stevens prepared the first extensive review on the use of "Organosilicone Surfactants as Adjuvants for Agrochemicals." It was suggested that oil spreading for insect control and improved foliage coverage might be enhanced by organosilicones, but no studies were referenced nor were any oils cited. Pesticide Science, pp. 103-122, 1993(38).

Policello et al. reported the use of low molecular weight alkyloligosiloxanes as additives for spray oil applications with vegetable and mineral oils (see Policello et al., Alkylsilicones for Agricultural Oils and Oil-Based Formulations, *Fourth International Symposium on Adjuvants for Agrochemicals, Melbourne, Australia,* 3-6 *Oct.* 1995, FRI Bulletin No. 193), pgs 303-307.) However, the alkyloligosiloxanes described therein were of low molecular weight (350-500 g/mol) with short silicone chains such as trisiloxanes, which are known to be key structural elements of silicone polyethers effective as adjuvants for aqueous spreading, whereas higher siloxane chains are generally known in the art to be less effective for spreading of aqueous compositions. Also, the described alkyloligosiloxanes do not have high silicone character.

Gaskin et al. reported the effect of unspecified alkylsiloxanes for improved spreading and efficacy of oil-based insecticidal sprays (Gaskin et al., Enhancement of plant and petroleum-derived spray oils with alkylsilicone surfactants, *Spray Oils—Beyond* 2000, pgs. 56-61, University of Western Sydney (2002). However, the alkylsiloxanes required relatively high use rates; further more no indication was there that the special effects of HSCAS were considered or investigated.

Murphy et al. (U.S. Pat. No. 5,561,099) refer to increasing the spreading properties of oil-containing compositions by adding to the composition a linear alkylsilicone of the formula:

$$(CH_3)_3Si—O—(Si(CH_3)_2O)_x—Si(CH_3)(R)O)_y—Si(CH_3)_3$$

or a cyclic alkylsilicone compound:

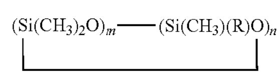

where x is an integer from 0 to 20, y is an integer from 1 to 10, m is an integer from 0 to 4, n is from 1 to 5 provided that m-f-n is from 3 to 5, and R is an alkyl group. These alkylsilicone compounds are used as adjuvants in preparing agricultural formulations which contain mineral or vegetable oils.

However, the compounds specified in detail are low molecular weight siloxanes with a low silicone character and as such not optimized for mineral oil-containing sprays.

U.S. Pat. No. 5,658,851, discloses lipophilic siloxanes which decrease the surface tension of oils. These siloxanes have the following general formula:

$$R_aMe_{(3-a)}Si\{OSiMe_2\}_x—\{OSiMeR\}_y—OSiMe_{(3-a)}R_a$$

where R is a lipophilic group selected from the group consisting of aryl, substituted aryl, aralkyl, alkyl phenyl ether, substituted phenylether, or alkyl alkyleneoxide groups; a is 0 or 1; x and y is 0 to 4 depending upon a, provided that the sum of x and y is greater than or equal to 6. Those siloxanes are referred to be adjuvants in oil-based herbicidal, disease treatment, or insecticidal compositions.

However, again the compounds described are low molecular weight siloxanes with a low silicone character which are not optimized for mineral oil containing sprays.

Finally, Murphy et al. (U.S. Pat. No. 5,658,852) disclose that one can increase the spreading properties of oil-containing pesticidal compositions by adding to the composition a linear alkylsilicone of the formula:

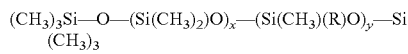

wherein x=0 to 20, y=1 to 10 and R and alkyl or alkyl ester group containing 6 to 18 carbons.

However, this as well as the previous patents does not recognize the benefit of alkylpolysiloxanes with high silicone character in mineral oil-containing formulations; the siloxanes referred to in Murphy are only effective in relatively high consumption rates, and do not perform well with mineral oils.

Kennedy et al. (U.S. Pat. No. 6,669,949) refers to asymmetrical polyether alkyl polysiloxanes with good oil compatibility and spreading. However, these asymmetrical alkyl polyether siloxanes are uneconomical to use due to difficult and cost intensive manufacturing processes such as those requiring expensive alkyllithium reagents, and they provide only moderate benefits in the spreading of mineral oils.

In 2004, Gaskin et al. reported the used of alkylsilicone adjuvants with a vegetable oil and potash to improve the evenness and efficiency of drying sultana grapes and reported that alkylsilicone adjuvants could reduce surface tension of a vegetable-based drying oil and increase the spreading of an oil emulsion on grapes (see Gaskin et al., *Proceeding of the 7th International Symposium on Adjuvants for Agrochemicals* (ISAA 2004), 8-12 Nov. 2004 (Cape Town, South Africa) pgs. 24-29).

However, the drying compositions of Gaskin are not suitable for general agrochemical use as the drying compositions required the use of potash which significantly increased the pH of the composition. Moreover, the degree of spreading was dependent on the ratio of potash to oil and the emulsion compositions of Gaskin required that the alkylsilicone adjuvant be mixed with oil prior to emulsification with water. Pesticidal oil compositions or mineral oil-based compositions were not considered in this study.

Nakanishi et al. (US Patent Application Publication 2005/0261133) refers to low molecular weight siloxanes with a low silicon character and hydrophilic glycerol substituents for enhanced oil spreading.

Sieverding et al. (US Patent Application Publication 2005/0244357) refer to a solvent-containing emulsifiable formulation substantially free of water, comprising at least one or more organic solvents, one or more emulsifier and one or more agriculturally acceptable active agents, and a formulation synergist comprising one or more polyether or alkyl modified siloxanes. It was discovered that low molecular weight polyether modified siloxanes without unmodified polydimethylsiloxane units were especially efficient. Siloxanes with high silicone character were not investigated, and no effort was done to find adjuvants which are especially efficient in mineral oil-containing formulations.

Therefore, a need still exists in the art for oil-based, e.g. mineral oil or vegetable oil-based agrochemical compositions which produces a decrease in surface tension and increase in spreading, minimize the amount of oil used while retaining the effectiveness of their agrochemical effects, and maintains an agrochemically acceptable pH.

DESCRIPTION OF THE INVENTION

Surprisingly, the problem of developing a oil-based, especially mineral oil-based, agrochemical composition which maximizes the efficiency of oil use is solved by practicing the instant invention.

The invention describes agrochemical oil compositions comprising:
(i) at least one alkylpolysiloxane of high silicone character,
(ii) at least one oil, and optionally
(iii) one or more agrochemically active compounds, emulsifiers and other agrochemically acceptable ingredients.

In one embodiment of the invention, the agrochemical oil compositions are free of potash.

In another embodiment of the invention, the pH of the oil composition is about 4.0 to about 9.0.

As noted above, the alkylpolysiloxanes of high silicone character (HSCAS) refer to alkylpolysiloxanes which have blocks of unmodified polydimethylsiloxane segments in their molecular structure, i.e. at least 10 uninterrupted polydimethylsiloxane groups (-Me$_2$SiO—) on average, and having hydrocarbon radicals providing compatibility with the oil.

In one embodiment of the invention, the alkylpolysiloxanes of high silicone character are represented by the siloxane (a) of formula (I):

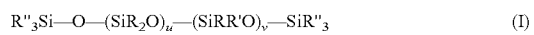

wherein:
R is a linear or branched alkyl radical with 1 to 4 carbon atoms,
R' is an aliphatic linear or branched alkyl radical containing 10-24 carbons,
R" is independently R or R',
u is 20 to 300,
v is 2 to 30, provided that u/v is greater or equal to 10; or the siloxane (b) according to EP 1 679 335 (U.S. Patent Application Publication 2006-155090), which is obtained by a reaction comprising of reacting
(A) an organopolysiloxane of formula (II)

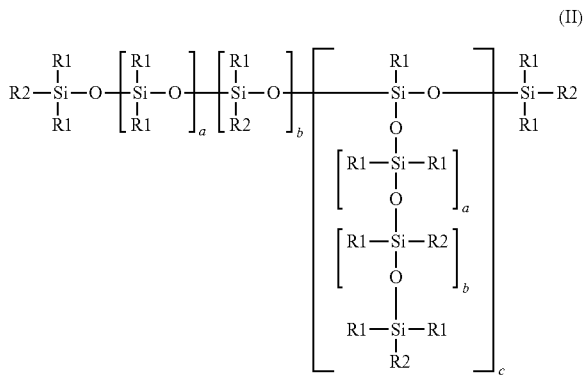

wherein:
R1 is identical or different aliphatic or aromatic hydrocarbon radicals with 1-20 C atoms, R2 is R1 or H, provided that at least three radicals R2 of the organopolysiloxane of formula (III) are hydrogen,
a is 5-500,
b is 1-50,
c is 0-5;
with a vinylsiloxane of formula (III)

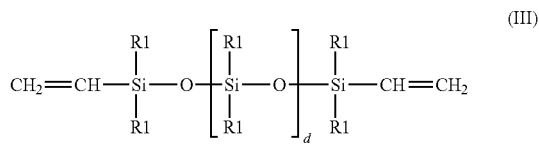

wherein d is 10 to 1000 and R1 is as defined above,
in the presence of Pt or Rh catalysts, provided that the organopolysiloxane (II) is present in at least 6-fold molar excess, preferably 6-60 fold molar excess of the vinylsiloxane (III), to produce the reaction product (A); and
a subsequent reaction with reaction product (A) with one or a combination of the following reactions (B) and (C):
(B) a transition metal-catalyzed partial or complete addition of the SiH groups to alkenyl and/or alkynylfunctional compounds, or
(C) under utilization of a catalyst, partial or complete conversion of the SiH groups remaining after reactions (A) and (B) with at least one alcohol from the group of linear or branched, saturated mono/polyunsaturated, aromatic, aliphatic/aromatic, potentially halogen-containing monofunctional alcohols, monofunctional polyether alcohols, monofunctional polyester alcohols, aminoalcohols.

Alkylpolysiloxanes of siloxane (a) are characterized by a ratio of unmodified to modified polydimethylsiloxane unit of greater or equal to 10:1, e.g. 10:1 to 25:1; 10:1 to 50:1 or 10:1 to 100:1, ensuring that on average the polymer contains uninterrupted block as of at least 10 unmodified polydimethylsiloxane units in the polymer distribution, which is a key factor to providing low surface tension and good spreading behavior to the agrochemical oil composition.

In one embodiment of the alkylpolysiloxanes of siloxane (a), the radicals R and R" are methyl, R' is 14-18 alkyl, u is 50-150, v is 3-10. In another embodiment of the alkylpolysiloxanes of formula (I), the ratio u/v is selected from the group consisting of about 15 to about 25; about 12 to about 50 and about 10 to about 150.

In alkylpolysiloxanes of siloxane (b), the high silicone character necessary for good spreading and low surface tension is imparted by the uninterrupted unmodified polydimethylsiloxane chain of the divinylsiloxane crosslinker (III), while the alkyl modified branches provide good compatibility with the oil.

One embodiment of the alkylpolysiloxanes of siloxane (b) is derived by complete conversion of the remaining SiH groups of the primary reaction product in a transition metal-catalyzed hydrosilylation reaction with monounsaturated linear or branched aliphatic olefins with 8-24 carbon atoms. In another embodiment of the invention, the terminal olefins have 12-18 carbon atoms. In still another embodiment of the invention, the terminal olefins have 16-18 carbon atoms. In still another embodiment, the transition metal catalyst is a platinum derivative.

In another embodiment the alkylpolysiloxanes of siloxane (b) is derived by complete conversion of the remaining SiH groups of the primary reaction product in a transition metal-catalyzed hydrosilylation reaction with a mixture of at least 80 mol % monounsaturated linear or branched aliphatic olefins with 8-24 carbon atoms, and up to 20 mol % of alkyl or alkynylfunctional aromatic compounds selected from the group of unsaturated hydrocarbons, unsaturated olefins bearing 1-4 additional substituents selected from he group of hydroxy groups, halogen groups, alkoxy groups, aminogroups, alkylsubstituted amino groups or ester groups, allylfunctional or vinyl-functional polyethers comprised of ethylene oxide, propylene oxide, butylene oxide and mixtures thereof, with the free end groups selected from the group of saturated alkyloxy, free hydroxy or hydroxy groups esterified with C1-C4 alkanoic acids.

In still another embodiment, the transition metal catalyst is a platinum derivative.

In another embodiment of the alkylpolysiloxanes of siloxane (b), R1 is methyl, a is 10 to 100, b is 2 to 30, c is 0; and d is 30-300.

In one embodiment of the invention, the HSCAS reduces the surface tension of the oil by more than 5 mN/m.

In another embodiment of the invention, the HSCAS increases area spread coverage on hydrophobic surfaces such as polymer films or plant foliage by a factor of about 2 or more compared to the corresponding compositions comprising no siloxane. In another embodiment of the invention the increase in area spread coverage is from selection from the ranges consisting of about 2 to about 15, about 2 to about 5, about 2 to about 3.5 and about 5 to about 15.

In an additional embodiment of the invention, compositions comprising HSCAS increase the foliage coverage which allows for the oil component in the composition to be reduced by 10-60% compared to a composition with HSCAS. In a further embodiment, compositions comprising HSCAS, the spray volume is reduced by 5 to 50% as compared to a necessary spray volume to achieve coverage of a composition without HSCAS. The agrochemical oil composition of the invention also comprise at least one mineral oil from the group of paraffinic, isoparaffinic, cycloparaffinic or naphthenic oils. Although not intended to be totally inclusive, exemplary mineral oils are those marketed under the tradenames BANOLE® from Total, ORCHEX® from Calumet, SUNSPRAY® from SUNOCO, SPRAYTEX® from TEXACO, EXXSOL® and ISOPAR® from Exxon Chemical, blends of mineral oils and emulsifiers such as STYLET-Oil® from JMS Flower Farms.

In another embodiment of the invention, if the (i) at least one alkylpolysiloxane of high silicone character is an alkylpolysiloxane of siloxane (b), then (ii) may further encompass other oils such as plant oils like soybean oil, coconut oil, canola oil, castor oil, palm oil, palm kernel oil, olive oil, corn oil, cottonseed oil, peanut oil, sesame oil, avocado oil, linseed oil, sunflower oil, jojoba oil, rapeseed oil, safflower oil, and the like, methylated and ethylated seed oils such as methyl cocoate, methyl palm kernel oil, methyl sunflowerate, palm oil methyl ester, methyl rapeate, methyl canolate, methyl soyate, methyl oleate, ethylated oleic acid, ethylated palmitic acid, methylated and ethylated soybean oil, canola oil, coconut oil, sunflower oil, corn oil, cottonseed oils.

Mixtures of mineral, vegetable and/or alkylated oils may be used when the at least one alkylpolysiloxane of high silicone character is an alkylpolysiloxane of formula (II).

The agrochemical composition described herein may optionally comprise one or several agrochemically active ingredients, such as acaricides, algicides, amino acid synthesis inhibitors, attractants, repellents, bactericides, biostimulants, cell wall inhibitors, fertilizers, fungicides, growth promoters, growth regulators, herbicides, insecticides, lipid biosynthesis inhibitors, miticides, molluscicides, nematicides, photosynthesis inhibitors, pigment inhibitors, plant growth regulators, rodenticides, safeners, sterilants, synergists, viricides, and which are used alone or in combinations thereof.

Chemical classes, compounds of active ingredients or organisms which are agriculturally acceptable are, together with their use or uses, are listed for example in The Pesticide Manual, 14$^{th}$ edition, 2006, The British Crop Protection Council, in The Manual of Biocontrol Agents, 3rd edition, 2004, The British Crop Protection Council, and in other there cited literature; these documents are also herein incorporated by reference.

The following are representative, but nonlimiting examples of agrochemically active compounds that can be used in the compositions of the invention. Examples of herbicidally active materials include but are not limited to acetochlor, acifluorfen, aclonifen, acrolein, alachlor, ametryne, aminopyralid, amitrole, asulam, atrazine, benazolin, bensulfuron-methyl, bentazon, benzobicyclon, benzofenap, bialaphos, bifenox, bromacil, bromobutide, bromofenoxim, bromoxynil, butachlor, butafenacil, chlomethoxyfen, chloramben, chloroacetic acid, chlorbromuron, chlorimuron-ethyl, chlorotoluron, chlomitrofen, chlorotoluron, chlorthal-dimethyl, clomazone, clodinafop, clopyralid, clomeprop, cyanazine, 2,4-D, 2,4-DB, daimuron, dalapon, desmedipham, desmetryn, dicamba, dichlobenil, dichloroprop, diclofop, difenzoquat, diflufenican, dimefuron, dimethachlor, dimethametryn, dimethenamid, dinitramine, diquat, diuron, endothall, ethametsulfuron-methyl, ethofumesan, fenac, fenclorim, fenoxaprop, fenoxapropethyl, flamprop-methyl, flazasulfuron, fluazifop, fluazifop-p-butyl, flumetsulam, flumiclorac-penyl, fluoroglycofen, flumetsulam, flumeturon, flumioxazin, flupoxam, flupropanate, fluridone, fluroxypyr, flurtamone, fomasafen, fosamine, glufosinate, glyphosate and its salts thereof, (such as alkyl ammonium or group I metal salts), haloxyfop, imazameth, imazamethabenz, imazamox, imazapic, imazapyr, imazaquin, imazethapyr, ioxynil, isoproturon, isoxaben, isoxaflutole, isoxapyrifop, lactofen, lenacil, linuron, MCPA, MCPB, mecoprop, mefenacet, mesotrione, metazachlor, methabenzthiazuron, metalachlor, methylarsonic acid, metolachlor, metobenzuron, metosulam, metamitron, naproanilide, naptalam, neburon, nicosulfuron, nonanoic acid, norflurazon, oryzalin, oxadiazon, oxyfluorfen, paraquat, pendimethalin, phenmedipham, picloram, picolinafen, pretilachlor, prodiamine, prometon, prometryn, propachlor, propazine, propisochlor, propyzamide, pyrazolate, pyrazolynate, pyrazosulfuron-ethyl, pyributicarb, pyridate, quinclorac, quizalofopethyl, quizalofop-P, quinclorac, rimsulfuron, siduron, simazine, simetryn, sulcotrione, sulfamic acid, a sulfonylurea, 2,3,6-TBA, tembotrione, terbumeton, terbuthylazine, terbutryn, trichloroacetic acid, triclopyr, trietazine, thenylchlor, thiazopyr, tralkoxydim, trietazine, trifuralin, salts thereof, or a mixture thereof.

Examples of fungicidally active compounds include but are not limited to aldemorph, azoxystrobin, benalaxyl, benomyl, bitertanol, borax, boscalid, bromocuonazole, sec-butylamine, captafol, captan, calcium polysulfide, carbendazim, chinomethionat, chlorothalonil, chlozolinate, copper and its derivatives, copper sulfate, cyprodinil, cyproconazole, dichlofluanid, dichlorophen, diclomezine, dicloran, diethofencarb, difenoconazole, dimethomorph, diniconazole, dithianon, epoxiconazole, famoxadone, fenarimol, fenbuconazole, fenfuram, fenhexamid, fenpiclonil, fenpropidin, fenpropimorph, fentin, fluazinam, fludioxonil, fluoroimide, fluotrimazole, fluqinconazole, flusulfamide, flutolanil, folpet, fosetyl, furalaxyl, guazatine, hexachlorobenzene, hexaconazole, hydroxyquinoline sulfate, imibenconazole, iminoctadine, ipconazole, iprodione, kasugamycin, kresoxim-methyl, mancozeb, maneb, mefenoxam, mepanipyrim, mepronil, mercuric chloride, metam, metalaxyl, metconazole, metiram, myclobutanil, nabam, nickel bis (dimethyldithiocarbamate), nuarimol, oxadixil, oxinecopper, oxolinic acid, penconazole, pencycuron, phthalide, polyoxin B, prochloraz, procymidone, propamocarb, propiconazole, propineb, pyrifenox, pyraclostrobin, pyrimethanil, pyroquilon, quintozene, spiroxamine, sulfur, tebuconazole, tecloftalam, tecnazene, thiabendazole, thifluzamide, thiophanate-methyl, thiram, tolclofos-methyl, tolylfluanid, triadimefon, triadimenol, triazoxide, tridemorph, trifloxystrobin, triforine, triticonazole, vinclozolin, zineb, ziram, salts thereof, or a mixture thereof.

In one embodiment of the invention, the fungicides are selected from the group consisting of aromatic fungicides, conazole fungicides (including triazole and imidazole fungicides), morpholine fungicides, polymeric dithiocarbamate fungicides, pyrimidine fungicides, spiro-ring containing fungicides, and strobilurin fungicides.

In yet another embodiment of the invention, the fungicides are selected from the group consisting of bitertanol, chlorothalonil, difenoconazole, epoxiconazole, mancozeb, maneb, propriconazole, pyrimethanil, spiroxamine, tebuconazole and tridemorph.

Examples of insecticidally actives compounds include but are not limited to abamectin, acephate, acetamiprid, acrinathrin, amitraz, azadirachtin, azamethiphos, azinphosmethyl, azocyclotin, bensultap, bifenthrin, bromopropylate, buprofezin, butoxycarboxim, cartap, chlorantriniliprole, chlorfenapyr, chlorfenson, chlorfluazuron, clofentezine, coumaphos, cyfluthrin, beta-cyfluthrin, lambda-cyhalothrin, cypermethrin, alpha-cypermethrin, theta-cypermethrin, cyromazine, DDT, deltamethrin, diafenthiuron, dicofol, dicrotophos, difenthiuron, diflubenzuron, dimethoat, emamectin benzoate, endosulfan, esfenvalerate, etoxazole, fenazaquin, fenbutatin oxide, fenoxycarb, fenpyroximate, fipronil, fluazuron, flubendiamide, flucycloxuron, flufenoxuron, tau-fluvalinate, formetanate, furathiocarb, halofenozide, gamma-HCH, hexaflumuron, hexythiazox, hydramethylnon, hydrogen cyanide, imidacloprid, lufenuron, methamidophos, methidathion, methiocarb, methomyl, methoxychlor, mevinphos, milbemectin, mineral oils, monocrotophos, nicotine, nitenpyram, novaluron, omethoate, organophosphorus compounds, oxamyl, oxydemeton-methyl, pentachlorophenol, phosphamidon, pymetrozin, permethrin, profenofos, pyridaben, rape seed oil, resmethrin, rotenone, spinetoram, spinosad, sulfluramid, tebufenozide, tebufenpyrad, tebupirimfos, teflubenzuron, tetrachlorvinphos, tetradifon, tetramethrin, thiamethoxam, thiocyclam, thiodicarb, tralomethrin, trichlorfon, triflumuron, trimethacarb, vamidothion, and salts thereof, or a mixture thereof.

Examples of plant growth chemicals include but are not limited to 6-benzylaminopurine, chlorflurenol, chlormequat, chlorphonium, cimectacarb, clofencet, cloxyfonac, cyanamide, cyclanilide, daminozide, dikegulac, ethephon, flumetralin, fluriprimidol, forchlorfenuron, gibberilic acid, inabenfide, indolylbutyric acid, 2-(1-naphthyl) acetamide, mefluidide, mepiquat, paclobutrazol, N-phenylphthalamic acid, thidiazuron, trinexapac-ethyl, uniconzole, salts thereof, or a mixture thereof.

The agrochemical composition described herein may optionally comprise other agrochemically acceptable ingredients commonly found in agrochemical compositions, such as emulsifiers, organic surfactants, viscosity modifiers, antifoams, solvents and the like and be in any form which can lead to spraying of the agrochemical composition of the invention. These agrochemically acceptable ingredients are described in standard reference texts such as *Chemistry and Technology of Agrochemical Formulations*, ed. D. A. Knowles, Kluwer Academic Publishers (1998) and *Controlled-Release Delivery Systems for Pesticides*, Herbert B. Scher, Marcel Dekker, Inc. (1999).

The current invention can be used with liquid formulation types which can be prepared essentially without water, such as emulsifiable concentrates (EC), suspension concentrates for direct application (SD), spot application (SA) or pour on (PO) formulations, oil dispersible powder (OP) formulations, oil miscible liquid (OL) formulations, oil miscible flowable concentrate (OF) formulations, oil dispersion (OD) or suspo-emulsion (SE) formulations, the formulation types are described by Crop Life International: Catalogue of pesticide formulation types and international coding system. Technical Monograph nr. 2, 5th edition. (http://www.croplife.org/library/documents/technical%20monographs/technical%20monograph%20N%C2%B02-%20March%202002.pdf) Accessed Nov. 17, 2003.

Surfactants and emulsifiers which may be optionally present in compositions according to this invention can be nonionic surfactants, anionic surfactants, cationic surfactants, amphoteric, zwitterionic, polymeric surfactants or any mixtures thereof.

The useful nonionic surfactants include alkoxylates, especially alkoxylated alcohols, alkoxylated fatty acids, especially ethoxylates and their derivatives including ethoxylated C8 to C24 saturated and unsaturated, linear and branched fatty acids or fatty alcohols, alkoxylated block copolymers, alkoxylated arylalkylphenols, especially ethoxylates and their derivates including alkylphenolethoxylates, alkoxylated amines, alkoxylated oils, fatty esters, especially polyethyleneglycol mono- and diesters of C8 to C24 saturated and unsaturated, linear and branched fatty acids, sorbitan derivatives including esters and ethoxylates, alkylpolyglucosides, and the like.

Typical ionic surfactants include alkylarylsulfonates, alkylarylsulfonic acids, carboxylated alcohol ethoxylates and alkylphenol ethoxylates, carboxylic acids/fatty acids, diphenylsulfonate derivatives, olefin sulfonates, phosphate esters, phosphorous organic derivatives, quaternary surfactants, sulfates and sulfonates of oils and fatty acids, sulfates and sulfonates of ethoxylated alkylphenols, sulfates of exthoxylated alcohols, sulfates of fatty acids, sulfonates of dodecyl and tridecylbenzenes, sulfonates of naphthalene and alkylnaphthalene, sulfonates of petroleum, sulfosuccinamates, alkanolamides, alkoxylated amines, N-acylsarocinates and the like.

An embodiment of the emulsifiers for this application are alkoxylated alcohols, alkoxylated alkylarylphenols and alkoxylated fatty acids, preferably of from 4 to about 50 ethylene oxide units and from 4 to 18 carbon atoms. Representative samples of ethoxylated arylalkyphenols are the TERGITOL® NP products from Dow-Union Carbide, of ethoxylated alcohols are TEGOALKANOL® TD products from Evonik-Goldschmidt, and of ethoxylated fatty acids is AROSURF® 8-190 from Evonik-Goldschmidt.

The agrochemical compositions according to this invention may comprise 0.01 to 99 vol. % of one or more of the alkylpolysiloxanes of siloxane (a) or siloxane (b), 1 to 99.99 vol. % of one or more oils, 0 to 30 vol. % of one or more agrochemically active ingredients, 0 to 15 vol. % of one or several emulsifiers, 0 to 95 vol. % of water and 0 to 50 vol. % of other inert ingredients.

A preferred range of agrochemical compositions according to this invention may comprise 0.1 to 5 vol. % of one or more alkylpolysiloxanes of siloxane (a) or siloxane (b), 10 to 60 vol. % of one or several oils, 0.5 to 20 vol. % of one or several agrochemically active ingredients, 0.1 to 6 vol. % of one or several emulsifiers, 20 to 85 vol. % of water.

A further preferred range of agrochemical compositions according to this invention may have reduced oil content and comprise 0.1 to 1 vol. % of one or more alkylpolysiloxanes of siloxane (a) or siloxane (b), 15 to 30 vol. %, of one or more paraffinic oil, vegetable oil or methylated vegetable oil, 2 to 15 vol. % of one or more agrochemically active ingredients, 0.1 to 3 vol. % of one or more emulsifiers, and 60-80 vol. % water.

As a result of the improved spreading and oil coverage of the HSCAS-comprising compositions of the present invention, a further embodiment of this invention is that reduced spray volumes can be achieved without reduced efficacy.

The agrochemical compositions according to this invention may be an emulsion (e.g. oil-in-water (O/W), water-in-oil (W/O), (W/O/W), (O/W/O), Pickering, microemulsion and nanoemulsions). In one embodiment of the invention, the emulsion is an O/W emulsion.

Preparation and types of emulsions are described in chapters 2 ("Emulsions—Properties and Production") and 3 ("Microemulsions, Vesicles and Liposomes") of Mollet et al., *Formulation Technology—Emulsions, Suspensions, Solid Forms*, Wiley-VCH, (2004), which is incorporated herein by reference.

The alkylpolysiloxanes of high silicone character may be present in the mixture of ingredients before the emulsification process or may be added to prepared emulsions of the other ingredients at a later time.

Alternatively, the agrochemical composition according to this invention may be a neat oil composition which is free of water or contains water in a range selected from the group consisting of less than 1%, less than 0.1%, less than 0.01% and less than 0.001% (all figures in vol. %)

In the method of producing the agrochemical compositions of the invention, the components can be added by any conventional means known in the art.

In another embodiment of the invention, the agrochemical compositions of the invention are especially useful for spraying mineral oil-containing agrochemical formulations by sprayers, which include but are not limited to handheld sprayers or via aerial application on plants.

Another embodiment of the invention is directed toward a method of treating plants against unwanted pests which comprises of administering a pesticidally effective amount of the agrochemical composition of the invention.

Another embodiment of the invention is directed toward a method of controlling unwanted weeds or treating plants against unwanted insects or disease, for example fungal, which comprises of administering a herbicidally, insecticidally or fungicidally effective amount of the agrochemical composition of the invention.

In another embodiment of the method of controlling unwanted weeds or treating plants, the agrochemical composition of the invention is administered on the stems, leaves, seeds or flowers of the unwanted weed or treated plant.

In yet another embodiment of the method of controlling unwanted weeds or treating plants, the agrochemical composition of the invention is administered on the leaves of the unwanted weed or treated plant.

In still another embodiment of the method of controlling unwanted weeds or treating plants, the agrochemical composition of the invention is administered on the leaves of the unwanted weed or treated plant which have a hydrophobic surface.

Leaves with hydrophobic corrugated surfaces can be difficult to wet and can hinder the full spreading of an agrochemical formulation over the whole leaf. The presence of alkylpolysiloxanes with high silicone character in the agrochemical compositions of the invention, provided a surprising and unexpected improvement in spreading as compared to previously used alkylpolysiloxanes and allows good coverage of the leaf.

In still another embodiment of the method of treating plants, the treated plant is of the genus Musa (e.g. bananas and plantains).

In still another embodiment of the invention, the agrochemical oil composition is administered to solid agrochemically active ingredients such as fungicides, herbicides, insecticides or fertilizers, to improve the handling properties and reduce the level of airborne particles.

In still another embodiment of the invention, the agrochemical oil composition is administered to treat seeds or to pesticidally treated seeds to enhance the coating properties.

It is well known in the art that improved coverage is beneficial for the efficacy of the spray. The presence of alkylpolysiloxanes with high silicone character in the compositions according to this invention may allow the reduction of the oil or active ingredient contents in the spray formulation with significant economical and ecological benefits without negatively affecting the biological effect, or the reduction of the overall spray volume.

The invention is further described by the following non-limiting examples which further illustrate the invention, and are not intended, nor should they be interpreted to, limit the scope of the invention.

EXAMPLES

Experimental Materials
Mineral Oils

BANOLE® HV oil, paraffinic distillate from hydrocracking process, Total Fluids, 76430 (Oudalle, France).

ORCHEX® 796 oil, hydrotreated light paraffinic distillate, Calumet Lubricants Co. (Indianapolis, Ind.).

SUNSPRAY® 6N oil, severely solvent refined heavy and/or only light paraffinic petroleum oils, Sunoco, Inc. (Philadelphia, Pa.).

STYLET-OIL®, severely hydrotreated paraffinic oil plus nonionic emulsification system, JMS Flower Farms, Inc., Vero Beach, Fla.

Methylated Vegetable Oils

AGNIQUE® ME 18 S-U, methyl soyate, Cognis Corporation, (Cincinnati, Ohio).

Fungicides

DITHANE® 60 SC is a commercial mancozeb fungicide provided by Dow Agrosciences (San Jose, Costa Rica).

CALIXIN® 86 OL is a commercial tridemorph fungicide provided by BASF Costa-Rica

Commercial Surfactants

TERGITOL™ NP-7 is a commercial nonylphenol ethoxylate available Dow-Union Carbide Corporation (Danbury, Conn.).

AROSURF® 8-190 is a commercial oleic acid ethoxylate available from Evonik-Goldschmidt Chemical Corporation (Hopewell, Va.).

Instrumentation

Digital Image Camera, Model DC200 from DAGI-MTI (Michigan City, Ind.).

Surface Tension

For the purposes of the present invention, interfacial tension is measured by the Wilhelmy plate method using a Krüss Processor Tensiometer K12 at 25° C.

HSCAS-1

HSCAS-1 is a siloxane (a) with high silicone character according to this invention, having a structure according formula (I) wherein R and R" is methyl, R' is hexadecyl, u is 83 and v is 5, wherein u/v is 16.6, which can be prepared in a method analogous to that described in U.S. Pat. No. 6,669,949, comparative example 7, by hydrosilylation of the corresponding SiH-functional siloxane (0.75 val/kg hydrogen) with 1-hexadecene in the presence of hexachloroplatinic acid.

HSCAS-2

HSCAS-2 is a siloxane (b) with high silicone character according to this invention, having a structure wherein R1 is methyl, which can be prepared in a method analog to that described in EP 1 679 335 (U.S. Patent Application Publication 2006-155090), example 2, by sequential hydrosilylation of a SiH-functional siloxane (3.5 val/kg hydrogen) with a) a vinylsiloxane of the structure $CH_2=CH-SiMe_2-O-[SiMe_2-O]_{348}-SiMe_2-CH=CH_2$, and b) 1-hexadecene, in the presence of a platinum catalyst.

LMAS-1 (Comparative)

Low Molecular Weight Siloxane (LMAS-1) is the siloxane described as AMS-1 in U.S. Pat. No. 5,561,099, example 1.

LMAS-2 (Comparative)

LMAS-2 is a low molecular weight alkylsiloxane commercially available from Momentive under the tradename Silwet 560, which is covered by U.S. Pat. Nos. 5,561,099 and 5,658,852 and corresponding foreign patents.

LSCAS-1 (Comparative)

LSCAS-1 is a Low Silicone Character Alkylsiloxane (i.e. having a ratio of u/v of less than 10), with a structure according to formula I, wherein R and R" is methyl, R' is hexadecyl, u is 2, v is 2, having a ratio of u/v of 1, which can be prepared analogous to the conditions described in example 1 of this invention from the corresponding SiH-functional siloxane and 1-hexadecene in the presence of a platinum catalyst.

LSCAS-2 (Comparative)

LSCAS-2 is a Low Silicone Character Alkylsiloxane (i.e. having a ratio of u/v of less than 10), with a structure according to formula I, wherein R and R" is methyl, R' is hexadecyl, u is 75, v is 25, having a ratio of u/v of 3, which can be prepared analogous to the conditions described in example 1 of this invention from the corresponding SiH-functional siloxane and 1-hexadecene in the presence of a platinum catalyst.

APES-1 (Comparative)

APES-1 is a mixture containing asymmetrical alkyl/polyether-modified siloxanes and is prepared as described in U.S. Pat. No. 6,669,949, example 8.

PES-1 (Comparative)

PES-1 is a is a commercial superspreading polyether-modified trisiloxane surfactant, available from Evonik-Goldschmidt Chemical Corporation (Hopewell, Va.) under the tradename BREAK-THRU® S 240, and covered by U.S. 2005/0244357 A1.

PES-2 (Comparative)

PES-2 is a commercial silicon polyether surfactant available from Evonik-Goldschmidt Chemical Corporation (Hopewell, Va.) under the trade name BREAK-THRU® OE 441, and covered by U.S. 2005/0244357 A1.

Example 1: Compositions Comprising Alkyl Siloxanes and Mineral Oils

This example exhibits the solubility of the oil spreaders and demonstrates that alkyl siloxanes with high silicone character (HSCAS) show excellent reduction of the surface tension of typical mineral oils to a significantly greater extent than for alkyl siloxanes with low molecular weight (LMAS) and/or low silicone character (LSCAS).

The siloxanes were mixed with the BANOLE HV and ORCHEX 796 at a concentration of 0.5 wt. % or with SUNSPRAY 6N at 1 wt. %.

TABLE 1

Surface tension and compatibility of HSCAS in oils

| Oil Type | No siloxane (control) | HSCAS-1 from Example 1 | HSCAS-2 from Example 2 | LSCAS-1 Comparative | LSCAS-2 Comparative | LMAS-1 Comparative | LMAS-2 Comparative |
|---|---|---|---|---|---|---|---|
| BANOLE HV | 29.1 | Clear 24.3 | Clear 21.9 | Clear 29.3 | Clear 27.8 | Clear 29.0 | Clear 28.5 |
| ORCHEX 796 | 30.1 | Clear 23.5 | Clear 22.2 | Clear 28.2 | Clear 28.4 | Clear 29.9 | Clear 29.9 |
| SUNSPRAY 6N | 29.5 | Clear 24.0 | Clear 22.1 | Clear 29.5 | Clear 28.2 | Clear 29.4 | Clear 29.4 |

The upper row in each field denotes the compatibility (clear=fully compatible), the second row the interfacial tension in mN/m.

Example 2: Compositions Comprising Alkyl Siloxanes and Methylated Vegetable Oils This example exhibits the solubility of the oil spreaders and demonstrates that alkyl siloxanes with high silicone character (HSCAS) show an excellent reduction of the surface tension of methylated vegetable oils, to a significantly greater extent than for alkyl siloxanes with low molecular weight (LMAS) and/or low silicone character (LSCAS).

The siloxanes were mixed with the methyl soyate at 1 wt. %.

TABLE 2

Comparison of Oil Compositions of High Silicone Character Alkyl Siloxanes With Low Silicone Character Alkyl Siloxanes or Low Molecular Weight Silicones

| Oil Type | No siloxane (control) | HSCAS-1 from Example 1 | HSCAS-2 from Example 2 | LSCAS-1 Comparative | LSCAS-2 Comparative | LMAS-1 Comparative | LMAS-2 Comparative |
|---|---|---|---|---|---|---|---|
| AGNIQUE ME 18S-U | 31.2 | Clear 23.8 | Clear 22.0 | Clear 29.0 | Clear 29.3 | Clear 30.4 | Clear 30.7 |

The upper row in each field denotes the compatibility (clear=fully compatible), the second row the interfacial tension in mN/m.

Example 3: Compositions Comprising Alkyl Siloxanes or Polyether Siloxanes and Oils This example demonstrates that HSCAS exhibit excellent compatibility and reduction of the surface tension of mineral and methylated vegetable oils, and to a significantly greater extent than observed with polyether siloxanes according to U.S. 2005/0244357 A1.

The siloxanes were mixed with the BANOLE HV and ORCHEX 796 at a concentration of 0.5 wt. % and with SUNSPRAY 6N and methylated vegetable oil at 1 wt. %.

TABLE 3

Comparison of Oil Compositions of High Silicon Character Siloxanes (HSCAS) and Polyether Siloxanes

| Oil Type | No siloxane (control) | HSCAS-1 Example 1 | HSCAS-2 Example 2 | BREAK-THRU PES-2 | BREAK-THRU PES-1 |
|---|---|---|---|---|---|
| Mineral Oils | | | | | |
| BANOLE HV | 29.1 | Clear 24.3 | Clear 21.9 | Separation N.D. | Separation N.D. |
| ORCHEX 796 | 30.1 | Clear 23.5 | Clear 22.2 | Separation N.D. | Separation N.D. |
| SUNSPRAY 6N | 29.5 | Clear 24.0 | Clear 22.1 | Separation N.D. | Separation N.D. |

TABLE 3-continued

Comparison of Oil Compositions of High Silicon Character Siloxanes (HSCAS) and Polyether Siloxanes

| Oil Type | No siloxane (control) | HSCAS-1 Example 1 | HSCAS-2 Example 2 | BREAK-THRU PES-2 | BREAK-THRU PES-1 |
|---|---|---|---|---|---|
| Methylated Vegetable Oil | | | | | |
| Methylated Vegetable Oil | 31.2 | Clear 23.8 | Clear 22.0 | Clear 26.2 | Clear 31.1 |

The upper row in each field denotes the compatibility (clear=fully compatible), the second row the interfacial tension in mN/m.

The polyether siloxanes according to U.S. 2005/0244357 A1 are incompatible with the paraffinic mineral oils. In methylated vegetable oil, these polyether siloxanes reduce the surface tension significantly less efficiently than achieved in compositions comprising HSCAS.

Example 4: Spreading of Siloxanes with Mineral Oil on Film

The spreading performance of compositions of the invention with a mineral oil is evaluated on polyester transparency film from Hewlett Packard (HP C3834A). Spreading is determined by applying 50 µL drops of the mineral oil composition onto the side with coarser texture of the film sheet using a micropipette and measuring the spread diameter. For the BANOLE HV paraffin oil, spread diameters are measured with a ruler after 15 minutes and the data is tabulated in TABLE 4.

TABLE 4

Comparison of Spreading of Alkyl Siloxanes with High Silicone Character (HSCAS) with Polyethersiloxanes, Alkylpolyethersiloxanes (APES) and Low Silicone Content Alkyl Siloxanes (LSCAS) on Polyester Film

| Additive | Spread Diameter (mm) |
|---|---|
| None | 11 |
| HSCAS-1 | 24 |
| HSCAS-2 | 36 |
| LMAS-1 | 12 |
| LMAS-2 | 13 |
| LCAS-1 | 12 |
| LCAS-2 | 15 |
| APES-1 | 14 |
| PES-1 | Incompatible |
| PES-2 | Incompatible |

It is demonstrated that mineral oil compositions comprising HSCAS have excellent spreading properties and are superior compared to compositions comprising PES, APES, and LSCAS siloxanes.

Example 5: Spreading of Siloxanes with Fatty Esters on Film

The spreading performance of compositions of the invention with a methylated vegetable oil is evaluated on polyester transparency film from Hewlett Packard (HP C3834A). Spreading is determined by applying 50 µL drops of the methylated vegetable oil composition onto the side with coarser texture of the film sheet using a micropipette and measuring the spread diameter. For the methylated vegetable oil, spread diameters are measured with a ruler after 10 minutes and the data are tabulated in TABLE 5.

TABLE 5

Comparison of Spreading of Alkyl Siloxanes with High Silicone Character (HSCAS) with Polyethersiloxanes, and Low Silicone Content Alkyl Siloxanes (LSCAS) on Polyester Film

| Additive | Spread Diameter (mm) |
|---|---|
| None | 10 |
| HSCAS-1 | 31 |
| HSCAS-2 | 33 |
| LMAS-1 | 10 |
| LCAS-1 | 13 |
| LCAS-2 | 22 |
| PES-1 | 10 |
| PES-2 | 15 |

It is demonstrated that compositions comprising alkylated vegetable oils and HSCAS have excellent spreading properties and are superior compared to compositions comprising PES and LSCAS siloxanes.

Example 6: Surface Tension and Spreading of Insecticidal Oil Compositions with Alkylpolysiloxanes of High Silicone Character (HSCAS)

Organic JMS Stylet-Oil® is a paraffinic oil registered for control of aphids, mites and other insects. The surface tension reduction and spreading performance of Stylet-oil compositions of this invention is presented in this example. The spreading performance is determined by applying 50 µL drops of the oil composition using a micropipette onto the underside of the polyester transparency film sheet (Hewlett Packard (HP C3834A)) and measuring the spread diameter with a ruler after 15 minutes. This information is compiled in Table 6.

TABLE 6

Spreading and Surface Tension of Stylet-Oil with HSCAS-1 and HSCAS-2

| Additive | Surface Tension, mN/m | Spreading, mm |
|---|---|---|
| None | 29.7 | 10 |
| HSCAS-1 | 24.0 | 23 |
| HSCAS-2 | 22.1 | 27 |
| LSCAS-1 | 29.3 | 11 |
| APES-1 | 24.0 | 14 |

It is demonstrated that insecticidal oil compositions comprising HSCAS show reduced surface tension and excellent spreading properties, and are superior compared to compositions comprising LSCAS and APES.

Example 7: Spreading of Mineral Oil Compositions Comprising Alkyl Siloxanes with High Silicone Character (HSCAS) on Banana Leaves Mineral oils provide protection against pests and disease in agrochemical applications. The improved spreading performance of mineral oil compositions of this invention on banana leaves is presented in this example. Spreading is determined by placing 0.5 µL drops of a blend of 0.5% siloxane in ORCHEX 796 oil between the veins of a banana leaf with a micropipette and capturing photos of the spread from a fixed camera at one minute intervals.

Spread Assignment:

In following TABLES no. 7, 8, 9, 11, 13, 15, 17 and 21 the area of spread is calculated by printing both images of comparative photographs in the same scale, followed by measuring the relative area of the drop as a rectangle in square millimeters. Due to the channeling effect of the raised veins of the leaf, the spreading of the compositions of this invention is generally rectangular in appearance. Based on the averaged values for each material evaluated, the following relative spread factors are provided:

1=No spreading
2=Intermediate spreading
3=Good/Very good spreading

TABLE 7

Comparison of Spreading of Alkyl Siloxanes with High Silicone Character (HSCAS), and Low Silicone Content Alkylsiloxanes (LSCAS) on Banana Leaves

| Additive | Spread Area, mm$^2$ Start | After 3 min. | Spread Assignment: |
|---|---|---|---|
| None | 149 | 149 | 1 |
| HSCAS-1 | 650 | 1075 | 3 |
| HSCAS-2 | 269 | 650 | 3 |
| LMAS-1 | 79 | 122 | 1 |
| LSCAS-1 | 72 | 90 | 1 |
| LSCAS-2 | 195 | 330 | 2 |

These data demonstrate the excellent spreading of oil compositions comprising mineral oils and HSCAS on corrugated leaf surfaces such as banana leaves, superior compared to compositions comprising LSCAS or LMAS.

Example 8: Spreading of Mineral Oil Compositions Comprising Alkyl Siloxanes with High Silicone Character (HSCAS) or Polyether Siloxanes on Banana Leaves Mineral oils provide protection against pests and disease in agrochemical applications. The improved spreading performance of paraffinic oil compositions of this invention on banana leaves is presented in this example. Spreading is determined by placing 0.5 μL drops of a blend of 0.5% siloxane in ORCHEX 796 oil between the veins of a banana leaf with a micropipette and capturing photos of the spread from a fixed camera at one minute intervals.

TABLE 8

Comparison of Spreading of Alkyl Siloxanes with High Silicone Character (HSCAS) with Polyethersiloxanes and Alkylpolyethersiloxanes on Banana

| Additive | Spread Area, mm$^2$ Start | After 7 min. | Spread Factor: |
|---|---|---|---|
| None | 97 | 97 | 1 |
| HSCAS-1 | 620 | 1505 | 3 |
| HSCAS-2 | 585 | 1750 | 3 |
| LMAS-1 | 91 | 96 | 1 |
| APES-1 | 310 | 695 | 2 |
| PES-2 | 96 | 96 | 1 |

These data demonstrate the excellent spreading of oil compositions comprising mineral oils and HSCAS on corrugated leaf surfaces such as banana leaves, superior compared to compositions comprising LMAS, APES or polyethermodified siloxanes.

Example 9: Spreading of Methylated Vegetable Oil Compositions Comprising Alkyl Siloxanes with High Silicone Character (HSCAS) on Banana Leaves This ability of HSCAS-1 and HSCAS-2 to promote spreading of a methylated vegetable oil on a leaf surface is demonstrated in this example. Spreading is determined by placing 0.5 μL drops of a blend of 1% siloxane in methylated vegetable oil between the veins of a banana leaf with a micropipette and capturing photos of the spread from a fixed camera at one minute intervals.

Photographs recorded at 2 minute intervals where HCAS-1 and HSCAS-2 are compared against Low Molecular Weight Siloxanes (LMAS-1 and LMAS-2).

TABLE 9

Spreading of Alkyl Siloxanes with High Silicone Character (HSCAS) on Banana Leaves

| Additive | Spread Area, mm$^2$ Start | After 2 min. | Spread Factor: |
|---|---|---|---|
| None | 173 | 207 | 1 |
| HSCAS-1 | 390 | 603 | 3 |
| HSCAS-2 | 270 | 710 | 3 |
| LMAS-1 (comparative) | 240 | 280 | 1 |
| LMAS-2 (comparative) | 216 | 271 | 1 |

These data demonstrate the excellent spreading of oil compositions comprising methylated vegetable oils and HSCAS on corrugated leaf surfaces such as banana leaves, superior compared to compositions comprising low molecular weight alkylsiloxanes.

Example 10: Improved Spreading of Compositions Comprising Mineral Oils, HSCAS and Fungicides Oil sprays for protection of banana plants may be aqueous emulsions of oil and one or more fungicides to control diseases such as black sigatoka. This example demonstrates that the alkyl siloxanes with high silicone character improve spreading of mineral oil emulsions containing fungicides. With HSCAS incorporated into the emulsions, the oil amount may be reduced by up to 50% without impairment of the spreading or leaf coverage of the fungicide and oil.

Table 10 lists the ingredients, order of addition and quantities for the emulsions tested for spreading capability. BANOLE HV oil, TERGITOL NP-7 emulsifier, CALIXIN® 86 OI tridemorph fungicide, and HSCAS-1 are first thoroughly blended with stirring, and then the water is slowly charged. The emulsion is agitated until uniform and ready for application.

TABLE 10

Tridemorph Fungicidal and BANOLE Oil Emulsions with HSCAS-1

| Additives | 10A vol. % | 10B vol. % | 10C vol. % | Standard-1 vol. % |
|---|---|---|---|---|
| BANOLE HV | 20% | 20% | 20% | 40% |
| CALIXIN® 86 OL | 2.5% | 2.5% | 2.5% | 2.5% |
| TERGITOL NP-7 | 0.2% | 0.2% | 0.2% | 0.4% |
| HSCAS-1 | 0.25% | 0.5% | 1% | — |
| Water | q.s. | q.s. | q.s. | q.s. |

Spreading of these oil/fungicide emulsions is determined by placing 0.1 μL drops between the veins of a banana leaf with a micropipette and capturing photos from a fixed camera at five minute intervals.

Incorporating a ruler with millimeter markings for reference, photographs confirm that addition of HSCAS-1 improves the spread area of the oil over the leaf surface and even surpasses the spread of a standard emulsion with twice the oil content.

TABLE 11

Spreading of Fungicidal Emulsions of Banole HV with HSCAS-1

| Material | Initial Area, mm² | Spread Area after 10 min, mm² | Spread Factor |
|---|---|---|---|
| Standard-1 | 69 | 86 | 1 |
| 10A (0.25% HSCAS-1) | 121 | 290 | 3 |
| 10B (0.5% HSCAS-1) | 79 | 234 | 3 |
| 10C (1% HSCAS-1) | 111 | 261 | 3 |

These data demonstrate the excellent spreading of emulsions comprising mineral oils, pesticides and HSCAS. The incorporation of a small amount of HSCAS unexpectedly provides superior spreading and leaf coverage even for compositions comprising a significantly reduced oil volume compared to typical oil compositions without HSCAS.

Example 11: Improved Spreading of Compositions Comprising Mineral Oils, HSCAS and Fungicides Oil sprays for protection of banana plants may be aqueous emulsions of oil and one or more fungicides to control diseases such as black sigatoka. This example demonstrates that oil emulsions comprising HSCAS spread to a greater extent than comparative compositions with LMAS, or compositions with twice the oil content. The composition of the oil and fungicide emulsions for this example are provided in Table 12 compared to LMAS-1. The emulsion compositions in Table 12 were prepared by the method described in Example 10.

TABLE 12

SUNSPRAY 6N and Tridemorph emulsions of HSCAS-1, HSCAS-2 and LMAS-1

| Materials (from left to right) | 11A vol. % | 11B vol. % | 11C Comparative vol. % | Standard-2 Comparative vol. % |
|---|---|---|---|---|
| SUNSPRAY 6N | 20% | 20% | 20% | 40% |
| TERGITOL NP-7 | 0.2% | 0.2% | 0.2% | 0.4% |
| HSCAS-1 |  | 0.25% |  |  |
| HSCAS-2 | 0.25% |  |  |  |
| LMAS-1 |  |  | 0.25% |  |
| CALIXIN ® 86 OL | 2.7% | 2.7% | 2.7% | 2.7% |
| Water | q.s. | q.s. | q.s. | q.s. |

Spreading is determined by placing 0.1 µL drops of the oil/fungicide emulsion between the veins of a freshly excised banana leaf with a micropipette and capturing photos of the spread from a fixed camera at five minute intervals.

Incorporating a ruler with millimeter markings for reference, photographs confirm that addition of HSCAS-1 and HSCAS-2 improves the spread area of the oil over the leaf surface and significantly surpasses the spreading of a standard emulsion with twice the oil content or the spreading of an emulsion with LMAS.

TABLE 13

Spreading of Fungicidal Emulsions of Sunspray 6N with HSCAS-1 and HSCAS-2

| Material | Initial Area, mm2 | Spread after 35 min, mm2 | Spread Factor |
|---|---|---|---|
| Standard-2 | 100 | 168 | 1 |
| HSCAS-2 (11A) | 217 | 812 | 3 |
| HSCAS-1 (11B) | 179 | 885 | 3 |
| LMAS-1 (11C, comparative) | 86 | 100 | 1 |

These data demonstrate the excellent spreading and leaf coverage of emulsions comprising mineral oils, pesticides and HSCAS, superior to compositions comprising LMAS.

Example 12: Spreading of Mineral Oil Emulsions Comprising Mancozeb and HSCAS Oil sprays for protection of banana plants may be aqueous emulsions of oil with one or more fungicides to control diseases such as black sigatoka. This example demonstrates that the alkylsiloxanes with high silicone character improve spreading of oil emulsions with mancozeb fungicide on banana leaves.

The emulsions compositions for this example are provided in Table 14. The BANOLE HV paraffinic oil is blended with the siloxane and TERGITOL NP-7 emulsifier. Water 1 is added to prepare the emulsion, and the DITHANE 60 SC mancozeb fungicide is then slowly dispersed. The second water aliquot is added, and the emulsion is mixed continuously to suspend the mancozeb prior to application.

TABLE 14

Mancozeb Fungicidal and SUNSPRAY 6N Emulsions with HSCAS-1 and HSCAS-2 at Reduced Oil Levels

| Additives | 12A vol. % | 12B vol. % | Standard-3 vol. % |
|---|---|---|---|
| SUNSPRAY 6N | 20% | 20% | 40% |
| HSCAS-1 |  | 0.25% |  |
| HSCAS-2 | 0.25% |  |  |
| TERGITOL NP-7 | 0.2% | 0.2% | 0.4% |
| Water 1 | 40% | 40% | 40% |
| DITHANE ® 60 SC | 2.5% | 2.5% | 2.5% |
| Water 2 | q.s. | q.s. | q.s. |

Spreading is determined by placing a 0.1 µL drop of the oil/fungicide emulsion between the veins of a freshly excised banana leaf with a micropipette and capturing photos of the spread from a fixed camera at five minute intervals.

Incorporating a ruler with millimeter markings for reference, photographs confirm that addition of HSCAS-1 and HSCAS-2 improves the spread area of the oil over the leaf surface and surpasses the spread of a standard emulsion with twice the oil content.

TABLE 15

Spreading of Mancozeb Fungicidal and SUNSPRAY 6N Emulsions with HSCAS-1 and HSCAS-2

| Material | Initial Area, mm² | Spread after 60 min, mm² | Spread Factor |
|---|---|---|---|
| Standard-3 | 109 | 187 | 2 |
| HSCAS-1 (12B) | 126 | 552 | 3 |
| HSCAS-2 (12A) | 151 | 768 | 3 |

The data show that alkyl siloxanes with high silicone character are highly effective for spreading of fungicidal oil emulsions with reduced oil content.

The enhanced spreading with HSCAS successfully compensates for the oil reduction of 50% in the emulsions.

Example 13: Spreading of Emulsions Comprising Mineral Oils, HSCAS and Pesticides on Leaves Positioned at a 10 Degree Slope Oil sprays for protection of banana plants may be aqueous emulsions of oil containing one or more fungicides to control diseases such as black sigatoka. This example demonstrates that the alkyl siloxanes with high silicone character improve spreading of oil with emulsions which contain a combination of tridemorph and mancozeb fungicides.

The emulsion compositions of this example and the order of addition of the additives are listed in Table 16.

TABLE 16

Tridemorph and Mancozeb Emulsions with BANOLE HV and HSCAS-1

| Additives | 13A vol. % | 13B vol. % | 13C vol. % | 13D vol. % | Standard-4 vol. % |
|---|---|---|---|---|---|
| BANOLE HV | 20% | 20% | 20% | 20% | 40% |
| TERGITOL NP-7 | 0.2% | 0.2% | 0.2% | 0.2% | 0.4% |
| Water 1 | 30% | 20% | 30% | 20% | 30% |
| CALIXIN ® 86 OL | 2.7% | 2.7% | 2.7% | 2.7% | 2.7% |
| DITHANE ® 60 SC | 8% | 8% | 8% | 8% | 8% |
| HSCAS-1 | 0.1% | 0.2% | 0.4% | 0.8% | |
| Water 2 | q.s. | q.s. | q.s. | q.s. | q.s. |

Spreading is determined by placing 0.1 µL drops of the oil/fungicide emulsion between the veins of a freshly excised banana leaf with a micropipette and capturing photos of the spread from a fixed camera at five minute intervals. The fresh leaf was fixed to a glass plate which was positioned at an angle of 10 degrees.

Incorporating a ruler with millimeter markings for reference, photographs confirm that addition of HSCAS-1 improves the spread area of the oil over the leaf surface and surpasses the spread of the standard emulsion with twice the oil content.

TABLE 17

Spreading of Banole HV Fungicidal Emulsions with a Concentration Range of HSCAS-1

| Material | Initial Area, mm2 | Spread after 20 min, mm2 | Spread Factor |
|---|---|---|---|
| Standard 4 | 93 | 152 | 2 |
| 13D (0.8% HSCAS-1) | 105 | 357 | 3 |
| 13C (0.4% HSCAS-1) | 68 | 334 | 3 |
| 13B (0.2% HSCAS-1) | 93 | 348 | 3 |
| 13A (0.1% HSCAS-1) | 103 | 262 | 3 |

This example demonstrates the excellent spreading and leaf coverage of pesticidal oil compositions with reduced oil volume, comprising HSCAS, on corrugated and non-flat leaf surfaces. It was unexpectedly observed that the finally covered leaf area extended upslope from the position of the original droplet on an angled leaf surface.

Example 14: Spreading of Emulsions Comprising Mineral Oil, Fungicides and HSCAS, Prepared with Different Addition Sequences This example demonstrates that HSCAS may be blended into fungicidal/oil compositions at different addition points without adversely affecting improved oil spreading performance. In Blend A in TABLE 10, the HSCAS-1 siloxane is added after the oil is first emulsified in water. In Blend B, it is present in the oil prior to emulsification in water.

TABLE 18

SUNSPRAY 6N and Fungicide Emulsions with Different order of Additions

| Standard 5 | | Standard 6 | |
|---|---|---|---|
| Order of Addition | % Additive vol. % | Order of Addition | % Additive vol. % |
| 1. | 20% SUNSPRAY 6N | 1. | 20% SUNSPRAY 6N |
| 2. | 0.2% TERGITOL NP-7 | 2. | 0.2% TERGITOL NP-7 |
| 3 | 25% Water | 3. | 0.2% HSCAS-1 |
| 4. | 2.7% CALIXIN ® 86 Ol | 4. | 25% Water |
| 5. | 0.2% HSCAS-1 | 5. | 2.7% CALIXIN ® 86 Ol |
| 6. | 8% DITHANE ® 60 SC | 6. | 8% DITHANE ® 60 SC |
| 7. | q.s. Water | 7. | q.s. Water |

Spreading is determined by placing 0.1 µL drops of the oil/fungicide emulsion between the veins of a freshly excised banana leaf with a micropipette and capturing photos of the spread from a fixed camera at five minute intervals. Using the millimeter scale on the reference ruler in these photos, differences in the spreading of the oils and fungicides are indistinguishable, so HSCAS-1 may be incorporated into the emulsions at multiple addition points.

TABLE 19

Spreading of Sunspray 6N Emulsions Prepared by Different Order of Additions of Components

| Material | Initial Area, mm2 | Spread after 30 min, mm2 |
|---|---|---|
| Standard 5 | 162 | 527 |
| Standard 6 | 162 | 532 |

The data show that the addition sequence of the HSCAS in the preparation of the fungicidal oil emulsions has no effect on the spreading performance.

Example 15: Emulsification of Oil and Tridemorph Fungicide with Nonionic Emulsifiers This example demonstrates that fungicidal oil compositions may be prepared with nonionic emulsifiers. The emulsion compositions and the order of introduction of components is presented in TABLE 20.

TABLE 20

ORCHEX 796 and Tridemorph Compositions with Different Emulsifiers

| Materials (from left to right) | 15A vol. % | 15B vol. % | 15C vol. % | Standard-7 vol. % |
|---|---|---|---|---|
| ORCHEX 796 | 20% | 20% | 40% | 40% |
| AROSURF 8-190 | 0.2% | | 0.4% | |
| TERGITOL NP-7 | | 0.2% | | 0.4% |
| Water 1 | 30% | 30% | 20% | 20% |
| CALIXIN ® 86 OL | 2.5% | 2.5% | 2.5% | 2.5% |
| HSCAS-1 | 1% | 1% | | |
| Water 2 | q.s. | q.s. | q.s. | q.s. |

Spreading is determined by placing 0.1 µL drops of the oil/fungicide emulsion between the veins of a freshly excised banana leaf with a micropipette and capturing photos of the spread from a fixed camera at five minute intervals. With the millimeter scale as reference in these photos, spreading of the oil and fungicide composition with AROSURF 8-190 is comparable to the composition with TERGITOL NP-7 with HSCAS-1 present at 1 vol. %. AROSURF 8-190 is a suitable as an emulsifier for these compositions.

TABLE 21

Comparison of Emulsifiers for Spreading of Orchex 796 and Fungicide Emulsions

| Material | Initial Area, mm2 | Spread after 30 min, mm2 | Spread Factor |
|---|---|---|---|
| Standard 7 | 50 | 62 | 1 |
| 15C | 52 | 56 | 1 |
| 15B (1% HSCAS-1) | 55 | 420 | 3 |
| 15A (1% HSCAS-1) | 49 | 388 | 3 |

The results show that emulsified oil compositions comprising HSCAS, nonionic emulsifiers (such as fatty acid ethoxylates or nonylphenol ethoxylates) pesticides, and a reduced oil volume show excellent spreading and leaf coverage, significantly higher than even for compositions comprising twice the amount of oil but without HSCAS.

Example 16: Control of Black Sigatoka Disease in Banana Plants with Mineral Oil Formulations Comprising Pesticides and HSCAS A field trial was conducted to evaluate the performance of oil sprays with HSCAS-1 siloxane of high silicone character and the fungicides THANE® 60 SC (mancozeb) and CALIXIN® 86 OL (tridemorph) on banana plants for control of black sigatoka disease. The rainfall intensity, particularly in the first 12 weeks of the 15 week trial, resulted in heavy black sigatoka disease pressure. This example demonstrates that incorporation of HSCAS into fungicidal sprays for bananas allows for oil reductions of up to 50% while maintaining control of black sigatoka disease.

The field trials and disease pressure evaluations were performed by a skilled experimenter. All treatments were applied weekly with a backpack sprayer at a 20 liters/hectare spray volume. A single row protocol of 10 banana plants was employed: however, only plants in the middle of the row were selected for weekly evaluation of disease. A row of 10 banana plants with no spray treatment was designated as the control.

The pesticide formulation contained 40% mineral oil (Spraytex M), 7.5% DITHANE 60 SC and 2.5% CALIXIN 86 OL. Cocktails which contained HSCAS-1 were comprised of 20% mineral oil and the same fungicide levels of mancozeb and tridemorph as the standard formulation. For reference, emulsions of 20% SPRAYTEX were prepared with the commercial levels of DITHANE 60 SC and CALIXIN 86 OL, but absent the HSCAS-1. The cocktails compositions and Row Number of Treatment are provided in TABLE 22.

TABLE 22

MINERAL OIL EMULSIONS comprising HSCAS-1 for Field Trials to Control BLACK SIGATOKA Disease

| | Row # | | | |
|---|---|---|---|---|
| Materials, l/ha | Untreated | 22A, standard | 22B | 22C |
| SPRAYTEX ® M | — | 8 | 4 | 4 |
| DITHANE ® 60 SC | — | 1.5 | 1.5 | 1.5 |
| CALIXIN ® 86 OL | — | 0.5 | 0.5 | 0.5 |
| Nonoxyl-7 | — | 0.08 | 0.04 | 0.04 |
| HSCAS-1 | — | — | — | 0.01 |
| Water | — | 10 | 14 | 14 |

Assessments of black sigatoka disease severity were recorded by a skilled experimenter using the Stover Scale modified by Gaulh (Gauhl F. 1994. Epidemiology and Ecology of Black Sigatoka (Mycosphaerella fijiensis Morelet) on Plaintain and Banana in Cost Rica, Central America. Translation of a 1989 PhD thesis originally in German, Unversitat Gottingen, Gottingen Germany). Evaluations started when the first treated leaf reached position number 4 and every 7 days thereafter until a week after the last application. Phytotoxicity was also monitored qualitatively. Disease severity is the most reliable parameter to measure differences between treatments. In the following tables, disease severity is determined by AUC (area under the curve). A statistical analysis using Tukey's multiple range test was performed, and, in the following table, averages with the same letter in the rating are not statistically different (P=0.05).

TABLE 23

BLACK SIGATOKA DISEASE SEVERITY RESULTS of FIELD TRIALS of MINERAL OIL EMULSIONS with FUNGICIDES and HSCAS-1

| Row Number | ml/ha Oil | ml/ha HSCAS-1 | Disease Severity | Rating |
|---|---|---|---|---|
| Untreated | — | — | 17.1 | B |
| 22A | 8000 | — | 2.1 | A |
| 22B | 4000 | — | 5.2 | AB |
| 22C | 4000 | 100 | 3.3 | A |

The disease severity and rating data show that there is an increase in black sigatoka disease when the oil is reduced from 8 liters to 4 liters/hectare in the spray emulsion. However, disease severity is significantly lower in formulations comprising reduced mineral oil content and HSCAS-1. These data demonstrate that HSCAS-1 allows for reduced oil content in fungicidal spray emulsions for control of black sigatoka disease in banana plants without negative effect on disease control.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:
1. An agrochemical oil composition comprising:
 (i) one or more alkylpolysiloxanes of high silicone character which have blocks of unmodified polydimethylsiloxane units in their molecular structure, the blocks having on average at least 10 uninterrupted polydimethylsiloxane units (-Me$_2$SiO—);
 (ii) one or more oils; and

(iii) optionally one or more agrochemically active compounds, emulsifiers and other agrochemically acceptable ingredients;
where the surface tension of the oil is reduced by the high silicon character alkylpolysiloxane at concentrations of only 1 wt. % of alkylpolysiloxane in the oil; and
wherein the one or more alkylpolysiloxanes of high silicone character comprise at least one alkylpolysiloxane selected from the group consisting of:
(1) a siloxane (a) of formula (I):

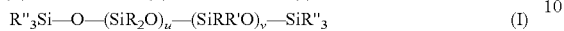

R"$_3$Si—O—(SiR$_2$O)$_u$—(SiRR'O)$_v$—SiR"$_3$  (I)

wherein:
R is methyl;
R' is an aliphatic linear or branched alkyl radical containing 10-24 carbons;
R" is methyl;
u is 20 to 300; and
v is 2 to 30;
provided that u/v is 10 to 25.

2. The agrochemical oil composition of claim 1;
wherein the one or more alkylpolysiloxanes of high silicone character further comprise at least one alkylpolysiloxane selected from the group consisting of:
(2) a siloxane (b) which is obtained by:
performing a reaction (i) comprising reacting an organopolysiloxane of formula (II) with a vinylsiloxane of formula (III) in the presence of Pt or Rh catalysts, provided that the organopolysiloxane (H) is present in at least 6-fold molar excess, of the vinylsiloxane (III), to produce a reaction product (i), wherein:
the formula (II) is:

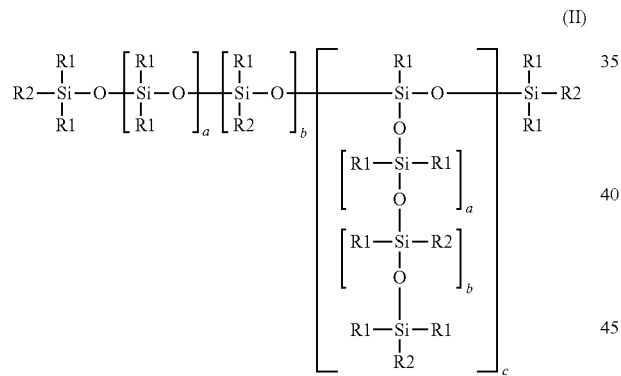

wherein:
R1 is methyl;
R2 is R1 or H, provided that at least three radicals R2 of the organopolysiloxane of formula (II) are hydrogen;
a is 10-500;
b is 1-50;
c is 0-5; and
the vinylsiloxane of formula (III) is:

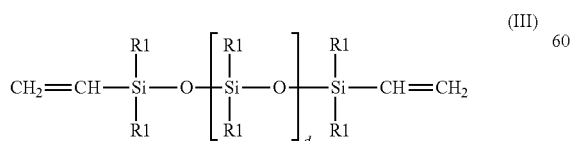

wherein d is 10 to 1000 and R1 is as defined above; and subsequently performing, with the reaction product (i), one or a combination of reactions (ii) and (iii);
wherein reaction (ii) is a transition metal-catalyzed partial or complete addition of the SiH groups to alkenyl and/or alkynylfunctional compounds; and
wherein reaction (iii) is under utilization of a catalyst, partial or complete conversion of the SiH groups remaining after reactions (i) and (ii) with at least one alcohol selected from the group consisting of linear or branched, saturated mono/polyunsaturated, aromatic, aliphatic/aromatic, potentially halogen-containing monofunctional alcohols, monofunctional polyether alcohols, monofunctional polyester alcohols, and aminoalcohols.

3. The agrochemical composition of claim 1;
wherein:
the one or more alkylpolysiloxanes are present in an amount of 0.01 to 99 vol. %;
the one or more oils are present in an amount of 1 to 99.99 vol. %;
the one or more agrochemically active compounds are present in an amount of 0 to 30 vol. %;
the one or more emulsifiers are present in an amount of 0 to 15 vol. %;
water is present in an amount of 0 to 95 vol. %; and
other inert ingredients are present in an amount of 0 to 50 vol. %.

4. The agrochemical composition according of claim 3;
wherein:
the one or more alkylpolysiloxanes are present in an amount of 0.1 to 5 vol. %;
the one or more oils are present in an amount of 10 to 60 vol. %;
the one or more agrochemically active compounds are present in an amount of 0.5 to 20 vol. %;
the one or more emulsifiers are present in an amount of 0.1 to 6 vol. %; and
water is present in an amount of 20 to 85 vol. %.

5. The agrochemical composition according of claim 3;
wherein:
the one or more alkylpolysiloxanes are present in an amount of 0.1 to 1 vol. %;
the one or more oils comprise one or more of a mineral oil, a vegetable oil, or a methylated vegetable oil present in an amount of 15 to 30 vol. %;
the one or more agrochemically active compounds are present in an amount of 2 to 15 vol. %;
the one or more emulsifiers are present in an amount of 0.1 to 3 vol. %; and
water is present in an amount of 60-80 vol. %.

6. The agrochemical composition of claim 1;
wherein the agrochemically active compound is a fungicide, herbicide, or insecticide.

7. The agrochemical composition of claim 1;
wherein the oil is a mineral oil, vegetable oil, or methylated vegetable oil.

8. The agrochemical composition of claim 1;
wherein:
R' is a 14-18 carbon alkyl;
u is 50-150; and
v is 3-10.

9. The agrochemical composition of claim 2;
wherein the oil is selected from the group consisting of a mineral oil, vegetable oil, and methylated vegetable oil.

10. The agrochemical composition of claim 9;
wherein the siloxane (b) is derived by complete conversion of the remaining SiH groups of the reaction product (i) in a transition metal-catalyzed hydrosilylation reaction with monounsaturated linear or branched aliphatic olefins having 8-24 carbon atoms.

11. The agrochemical composition of claim 10;
wherein the siloxane (b) is derived by complete conversion of the remaining SiH groups of the reaction product (i) in a transition metal-catalyzed hydrosilylation reaction with monounsaturated linear or branched aliphatic olefins having 16-18 carbon atoms.

12. The agrochemical composition of claim 9;
wherein the siloxane (b) is derived by complete conversion of the remaining SiH groups of the reaction product (i) in a transition metal-catalyzed hydrosilylation reaction with a mixture comprising:
at least 80 mol % monounsaturated linear or branched aliphatic olefins having 8-24 carbon atoms; and
up to 20 mol % of alkyl or alkynylfunctional compounds selected from the group consisting of:
unsaturated aromatic hydrocarbons;
unsaturated olefins bearing 1-4 additional substituents selected from the group consisting of hydroxy groups, halogen groups, alkoxy groups, amino groups, alkylamino groups, and ester groups; and
allyl-functional or vinyl-functional polyethers comprised of ethylene oxide, propylene oxide, butylene oxide, or mixtures thereof, with the free end groups selected from the group of saturated alkyloxy, free hydroxy or hydroxy groups esterified with C1-C4 alkanoic acids.

13. The agrochemical composition of claim 9;
wherein for the siloxane (b):
R1 is methyl;
a is 10 to 100;
b is 2 to 30;
c is 0; and
d is 30-300.

14. A method of controlling unwanted weeds or treating plants against pests, comprising:
administering a pesticidally effective amount of the agrochemical composition of claim 1 to a plant or weed.

15. A method of controlling unwanted weeds or treating plants against insects or disease, comprising:
administering a herbicidally, insecticidally or disease controlling effective amount of the agrochemical composition of claim 1 to a plant or weed.

16. The method of claim 15;
wherein the composition comprises a herbicide, fungicide, or insecticide.

17. The method of claim 15;
wherein the treatment is against unwanted fungi which comprises of administering a fungicidal effective amount of the agrochemical composition of claim 1.

18. The method of claim 17;
wherein the plant is banana or plantain.

19. The method of claim 18;
wherein the administration of the fungicidal effective amount of the agrochemical composition of claim 1 is on the foliage of the banana or plantain plant.

20. The agrochemical composition of claim 1;
wherein the agrochemical oil composition has a surface tension that is at least 15% lower than the one or more oils.

* * * * *